(12) United States Patent
Datta et al.

(10) Patent No.: US 8,759,047 B2
(45) Date of Patent: Jun. 24, 2014

(54) PROCESS FOR FERMENTATION OF SYNGAS FROM INDIRECT GASIFICATION

(75) Inventors: Rathin Datta, Warrenville, IL (US); Ralph Corley, Pensacola Beach, FL (US)

(73) Assignee: Coskata, Inc., Warrenville, IL (US)

(*) Notice: Subject to any disclaimer, the term of this patent is extended or adjusted under 35 U.S.C. 154(b) by 726 days.

(21) Appl. No.: 12/561,116

(22) Filed: Sep. 16, 2009

(65) Prior Publication Data

US 2010/0298450 A1   Nov. 25, 2010

(51) Int. Cl.
*C12P 7/06* (2006.01)

(52) U.S. Cl.
USPC .......................................................... 435/161

(58) Field of Classification Search
USPC .......................................................... 435/161
See application file for complete search history.

(56) References Cited

U.S. PATENT DOCUMENTS

| | | | |
|---|---|---|---|
| 4,336,335 A | 6/1982 | Muller et al. | |
| 4,597,777 A | 7/1986 | Graham | |
| 5,173,429 A | 12/1992 | Gaddy et al. | |
| 5,558,698 A | 9/1996 | Baker et al. | |
| 6,136,577 A | 10/2000 | Gaddy | |
| 6,183,703 B1 * | 2/2001 | Hsu et al. | 422/211 |
| 6,340,581 B1 | 1/2002 | Gaddy | |
| 6,755,975 B2 | 6/2004 | Vane et al. | |
| 6,899,743 B2 | 5/2005 | Wijmans et al. | |
| 6,919,488 B2 | 7/2005 | Melnichuk et al. | |
| 6,972,114 B2 | 12/2005 | Pope et al. | |
| 7,118,672 B2 | 10/2006 | Husain et al. | |
| 7,228,806 B2 | 6/2007 | Dueck et al. | |
| 7,285,402 B2 | 10/2007 | Gaddy et al. | |
| 7,375,142 B2 | 5/2008 | Pearson | |
| 7,465,844 B2 | 12/2008 | Suyama et al. | |
| 2003/0077771 A1 * | 4/2003 | Verser et al. | 435/161 |
| 2003/0211585 A1 * | 11/2003 | Gaddy et al. | 435/161 |
| 2005/0113467 A1 * | 5/2005 | Branson | 435/41 |
| 2007/0275447 A1 | 11/2007 | Lewis et al. | |
| 2008/0057554 A1 | 3/2008 | Huhnke et al. | |
| 2008/0093583 A1 * | 4/2008 | van den Oosterkamp et al. | 252/373 |
| 2008/0193989 A1 * | 8/2008 | Verser et al. | 435/161 |
| 2008/0216391 A1 * | 9/2008 | Cortright et al. | 44/307 |
| 2008/0305539 A1 | 12/2008 | Hickey et al. | |
| 2009/0029434 A1 | 1/2009 | Tsai et al. | |

(Continued)

FOREIGN PATENT DOCUMENTS

WO    WO2008154301    12/2008

OTHER PUBLICATIONS

Phillips et al. Thermochemical Ethanol via Indirect Gasification and Mixed Alcohol Synthesis of Lignocellulosic Biomass. National Renewal Energy Laboratory. Technical Report NREL/TP-510-41168. 132 Pages (Apr. 2007).*
U.S. Appl. No. 12/258,193, filed Oct. 24, 2008, Datta et al.

(Continued)

*Primary Examiner* — Michael Marcheschi
*Assistant Examiner* — Jonathan Hurst

(57) ABSTRACT

Ethanol and other liquid products are produced from biomass using indirect gasification of the biomass to produce a syngas containing CO2, CO, H2 and methane that passes the syngas without substantial removal of the methane to a fermentation zone for the conversion of the CO and CO2 and H2 to ethanol and the production of a methane rich stream followed by the methane reforming of the methane rich stream to produce additional CO and CO2 and H2 that passes to the fermentation zone.

13 Claims, 2 Drawing Sheets

(56) References Cited

U.S. PATENT DOCUMENTS

| | | | |
|---|---|---|---|
| 2009/0029446 A1* | 1/2009 | O'Rear | 435/262.5 |
| 2009/0035848 A1 | 2/2009 | Hickey et al. | |
| 2009/0104676 A1 | 4/2009 | Tsai et al. | |
| 2009/0162914 A1* | 6/2009 | Offerman et al. | 435/167 |
| 2009/0215139 A1 | 8/2009 | Datta et al. | |
| 2009/0215142 A1 | 8/2009 | Tsai et al. | |
| 2009/0215153 A1 | 8/2009 | Tsai et al. | |
| 2009/0215163 A1 | 8/2009 | Tsai et al. | |
| 2009/0286296 A1 | 11/2009 | Hickey et al. | |

OTHER PUBLICATIONS

Clausen, E.C., et al., "Ethanol From Biomass by Gasification/Fermentation", Presented at Plastics, Tires, Auto Wastes/Biomass MSW Symposium, Fall 1993, Chicago, 38 (3).

Klasson, K.T., et al., "Biological Production of Liquid and Gaseous Fuels from Synthesis Gas," Appl. Biochem. Biotechnol., vol. 24-25, No. 1, Mar. 1990, 857-873.

Vega, J. L., et al., "The Biological Production of Ethanol from Synthesis Gas," Appl. Biochem. Biotechnol. vol. 20-21, No. 1, Jan. 1989, 781-797.

Phillips, John R., et al., "Synthesis Gas as Substrate for the Biological Production of Fuels and Chemicals," Appl. Biochem. Biotechnol. vol. 45-46, No. 1, Mar. 1994, 145-157.

Barik, S., et al., "Biological Production of Alcohols from Coal Through Indirect Liquefaction," Appl. Biochem. Biotechnol. vol. 18, No. 1, Aug. 1988, 363-387.

Henstra, A. et al,, "Microbiology of synthesis gas fermentation for biofuel production," Current Opinion in Biotechnol., vol. 18, Mar. 2007, 200-206.

Abrini, J. et al., "*Clostridium autoethanogenum*, sp. nov., an anaerobic bacterium that produces ethanol from carbon monoxide," Arch. Microbiol. vol. 161, 1994, 345-351.

Das, A. and Ljungdahl, L.G., "Electron Transport System in Acetogens," Biochemistry and Physiology of Anaerobic Bacteria, 2003, 191-204, Springer-Verlag New York, Inc., New York, US.

Drake, H. and Kusel, K., "How the Diverse Physiologic Potentials of Acetogens Determine Their In Situ Realities," Biochemistry and Physiology of Anaerobic Bacteria, 2003, 171-190, Springer-Verlag New York, Inc., New York, US.

Grethlein, A. et al., "Evidence for Production of n-Butanol from Carbon Monoxide by *Butyribacterium methlyotrophicum*," J. Ferment. Bioeng., vol. 72, No. 1, 1991, 58-60.

Worden, R.M., et al., "Production of butanol and ethanol from synthesis gas via fermentation," Fuel. vol. 70, May 1991, 615-619.

U.S. Appl. No. 11/441,392, filed May 25, 2006, Lewis.

U.S. Appl. No. 11/514,385, filed Aug. 31, 2006, Huhnke.

Mark A. Paisley, Advanced Biomass Gasification for the Economical Production of Biopower, Fuels, and Hydrogen—Implementation in Montgomery, New York, pp. 1-4.

* cited by examiner

PROCESS FOR FERMENTATION OF SYNGAS FROM INDIRECT GASIFICATION

FIELD OF THE INVENTION

This invention relates to the production of synthesis gas and the biological conversion of CO and mixtures of $CO_2$ and $H_2$ to liquid products.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

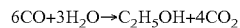

$$6CO + 3H_2O \rightarrow C_2H_5OH + 4CO_2$$

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol. Other products such as acetic acid and n-butanol have similar large stoichiometric requirements for the gases.

Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance.

As the theoretical equations show the components of the syngas primary inputs into the production of the desired products comprise CO and $H_2$ and $CO_2$, and the essential feed components for supply to the microorganisms comprise CO and $H_2$. The syngas bioconversion processes can specifically use the CO and H2/CO2 to high conversion to make products such as ethanol, acetic acid, butanol etc. Such bioconversion processes ordinarily operate at moderate pressures and low temperatures.

Direct gasification processes are well known in the production of syngas. Direct gasification processes use oxygen and/or electricity to generate plasma or molten salt/glass to achieve very high temperatures and good residence times to provide a syngas with very low concentrations of methane (~2% or lower) and very low tar (<100 ppm). Such processes primarily produce CO and H2/CO2 that are usable by the bioconversion processes. Direct gasifiers include updraft gasifiers and downdraft gasifiers and have the principle advantage of very simple design and direct heat transfer from the gases to the biomass. The principle disadvantage of direct gasification systems are the energy input for generating heat, particularly electrical energy for generating plasma in the case of plasma gasification and the supply of oxygen where the direct gasification is oxygen blown.

Indirect gasification technologies do not directly use oxygen or large amounts of electricity and are thus inherently have lower operating costs and capital. A typical type of indirect gasification is accomplished when a portion of the fuel (char) from the process gets combusted with air to generate the heat that is transferred by a heat transfer medium to the biomass feed to gasify or pyrolyze it to into the desired syngas product. Thus many indirect gasification technologies operate at lower temperatures, typically less than 900° C. in an oxygen starved atmosphere with substantial residence time and consequently produce considerable amounts of methane cannot be utilized by the organisms. However such gasification systems can be more economical both in capital and operating costs than the direct higher temperature gasification technologies because they do not use oxygen, electricity or other feeds such as coke.

The overall result is that many of these gasifiers have a lower temperature profile and residence time, but usually have much higher methane concentrations (10 to 15%) in the product gas. Methane is not usable in the biological conversion of the syngas to chemical products. Nevertheless achieving efficiency in the biomass conversion requires good utilization of the methane since a mole of methane has much higher (4×) energy content than CO or H2.

Separation of the methane for recovery from the syngas adds considerable process expense. First there is the cost of the extra separation equipment that must process the entire stream of syngas, of which the methane may comprise a minor portion, typically on the order of 20%, and often much less. Therefore the cost associated with the equipment and its operation to remove the methane from the raw syngas stream makes such recovery impractical.

It is also conventional to reform the raw syngas by catalytic processes by addition of oxygen as required to convert some of this methane to CO, H2/CO2. These processes operate at high temperatures and need considerable amount of gas recycling and separations. Also these processes again have to deal with the entire molar flow of the gas that is produced in the gasifier.

Conversion of this methane in the raw syngas by reforming or catalytic methods is being strongly pursued by many gasification technologies. However these technologies have to deal with the primary flow of the syngas from the gasifier, operate at very high temperatures and involve recycle and separations at these conditions. For example, U.S. Pat. No. 7,375,142 shows a process wherein two stages of Fischer Tropsch processes convert a syngas stream comprising carbon monoxide, carbon dioxide, hydrogen and methane, recovering carbon dioxide and hydrogen from the syngas for conversion to methanol in a first Fisher Tropsch reactor and sending the remainder of the syngas along with the methanol to provide a feed to a Fisher Tropsch reactor for the production of ethanol.

The methane content of such gasifiers is high and in the range of 10 to 15%. Considering that a mole of methane has 8 electrons compared to 2 electrons for either CO or H2, the equivalent of electrons contained in methane is almost as high as either the H2 or CO. Thus, for the energy content of the biomass feed to be efficiently utilized to make ethanol or other products, this methane needs to be converted to CO, H2/CO2 and fed to the bioconversion process.

SUMMARY OF THE INVENTION

It has been found that bioconversion processes can be used to simply and efficiently separate the methane from the syngas of an indirect gasifier. In this process methane containing syngas passes to the bioconversion process wherein it consumes the CO and H2/CO2 to a very high extent and the exhaust gas will be primarily methane and CO2. Use of the bioconversion process to consume the CO and H2/CO2 also has the advantage of providing the residual stream of methane and CO2 at conditions that are compatible with the separation of the CO2 and methane. Thus the methane and CO2 can be readily separated with only small adjustments to temperature and pressure. This allows the process to efficiently recover the methane in a methane rich stream while the CO2 is exhausted. At least some of the methane rich stream is then separately converted in a partial oxidation reformer to make good quality syngas containing CO and H2/CO2 which is then fed back to the fermentor to make more liquid product.

Thus, this invention enables the utilization of high methane containing syngas in a bioconversion processes to make ethanol or other fuels and chemicals. The high methane containing syngas has no adverse effects on the operation of the bioreactors, which efficiently convert the CO and H2/CO2 to the ethanol and other products. The additional mass volume of gas passing through system by virtue of the methane presence adds little to the cost of the bioreactors. The feed gas may pass through the bioreactor in single or multiple passes to consume CO and H2. The exhaust gas becomes predominantly methane and CO2 which are readily separated at conditions close to its exit conditions by several known technologies and preferably by membrane based technologies at temperatures and pressures that are very near that of the operations of the bioreactors. This methane rich stream is then separately reformed to make good quality syngas containing CO and H2/CO2 which is then fed back to the bioreactors enabling high degree of utilization of the original chemical energy of the feedstock.

Thus in one aspect this invention is a process for the production of liquid products from a carbonaceous feed by gasification of the feed to syngas comprising CO2, CO, H2 and CH4, followed by bio-conversion of syngas components. The process includes the steps of providing a carbonaceous feed to a gasifier and heating the carbonaceous feed to produce a syngas comprising CO2, CO, H2 and at CH4. The carbonaceous feed is preferably biomass and a portion of the biomass is used as fuel to indirectly heat the remainder of the biomass to produce syngas. The process passes a feed gas comprising syngas from the gasifier to a bioreactor to convert CO and CO2 and H2 to liquid products by contact with microorganisms therein. A bioreactor effluent stream containing the liquid products from the bioreactor is removed from the bioreactor and liquid products are recovered from the effluent stream. A tail gas stream is also recovered from the bioreactor that comprises CO2 and CH4. The process separates a portion of the CO2 from the tail gas stream to produce a CH4 rich gas stream and passes at least a portion of the CH4 rich stream to a partial oxidation reformer to produce a reformed gas stream comprising CO and CO2 and H2. At least a portion of the reformed gas stream passes to the bioreactor along with syngas from the gasifier to provide the feed gas to the bioreactor. The liquid products recovered from the bioreactor process will typically comprise at least one of ethanol, acetic acid, butanol, or butyric acid. The preferred liquid product for production from the process is ethanol.

The process can convert almost any solid carbonaceous source of material into usable liquid products. All materials that can produce syngas from lower temperature gasification processes are suitable for this invention. The invention may be useful for conversion of any carbonaceous feed into liquid products via fermentation. Suitable carbon sources include coke, coal and peat. Preferred carbon sources comprise biomass and include wood, miscanthus, switchgrass, sugar cane bagasse, corn stover. Other carbon sources can comprise construction and demolition debris along with urban waste.

The process will have significant advantage where the gasification process produces a substantial amount of methane. Typically the process finds good application where the syngas contains at least 5 mole % CH4 on an anhydrous basis. Generally, the syngas on an anhydrous basis comprises 20 to 45 mole % H2, 15 to 50 mole % CO, 10 to 20 mole % CH4, and 10 to 20 mole % CO2. The processing of the syngas through the bioreactor and producing liquid products will further concentrate the syngas. In the case where the syngas on anhydrous basis comprises at least 10 mole % CH4, the tail gas from the bioreactor will comprises at least 20 mole % CH4.and may comprise 25 mole % or more.

The process also offers the flexibility of using a portion of the CH4 for heat or power. Where the amount of methane is large or the energy value of the CH4 increases with respect to the needs of the plant, an increased portion of the CH4 rich stream can pass to a combustion heat recovery system for the generation of power or to provide process heat.

After separation the recovered methane undergoes reforming to produce additional amounts of CO and H2. Endothermic reforming of the methane may be practiced as is sometimes referred to as steam methane reforming. The preferred form of reforming is partial oxidation or autothermal reforming with the principle objective of producing additional quantities of CO and H2.

In a more specific form the invention is a process for the production of ethanol from a biomass feedstock by indirect gasification to syngas comprising CO2, CO, H2 and CH4, followed by bio-conversion of syngas components. The process comprises providing a biomass feedstock to a gasifier and indirectly gasifying the biomass feedstock by contact with a heating medium at a temperature of less than 1000° C. and a pressure of at least 4 bars absolute to produce a syngas stream comprising CO2, CO, H2 and at least 10 mole % of CH4 on an anhydrous basis. The process passes a feed gas comprising syngas from the gasifier to a bioreactor to convert CO and CO2 and H2 to ethanol by contact with microorganisms therein. A bioreactor effluent stream containing ethanol from the bioreactor is withdrawn and the ethanol is separated in an ethanol recovery section to produce an ethanol product. A tail gas stream from the bioreactor comprising on an anhydrous basis at least 40 mole % CO2 and 25 mole % CH4 undergoes separation of CO2 to produce a CH4 rich gas stream. A portion of the CH4 rich gas stream passes to a combustion heat recovery system for the generation of power or to provide process heat. Another portion of the CH4 rich stream passes to an autothermal reformer to produce a reformed stream comprising CO and CO2 and H2. At least a portion of the reformed stream passes to the bioreactor along with syngas from the gasifier to provide the feed gas to the bioreactor.

DETAILED DESCRIPTION OF THE INVENTION

Practical production of ethanol from biomass requires the effective coupling of four different zones. First a gasification zone that converts biomass into syngas, defined to mean at least one of CO or a mixture of CO2 and H2. A gas clean-up zone typically conditions the raw syngas by removal of contaminants to prepare it for the consumption by the microorganisms in the fermentation zone. Next, a fermentation zone, in the form of a bioreactor, receives the syngas feed and delivers it to the microorganisms that expel ethanol into fermentation liquid. Finally, a separation zone must recover ethanol from the broth in an energy efficient manner. The practice of this invention adds the step of reforming methane from the gasification step for use as an additional feed to the fermentation zone.

Since methane is not utilized in biological conversion processes for the production of liquid fuels, the common approach has been to focus on methods of generating syngas that maximize the production of CO and H2 while minimizing the production of unconvertible material like methane. This need to minimize methane production eliminates a number of available gasification technologies from consideration and can increase the cost of the gasification step. This invention recognizes that the high methane content syngas poses no significant drawbacks in the operation of the bioconversion zone while offering significant advantages in enabling the utilization of syngas processes that operate at lower temperatures.

Figure 1:
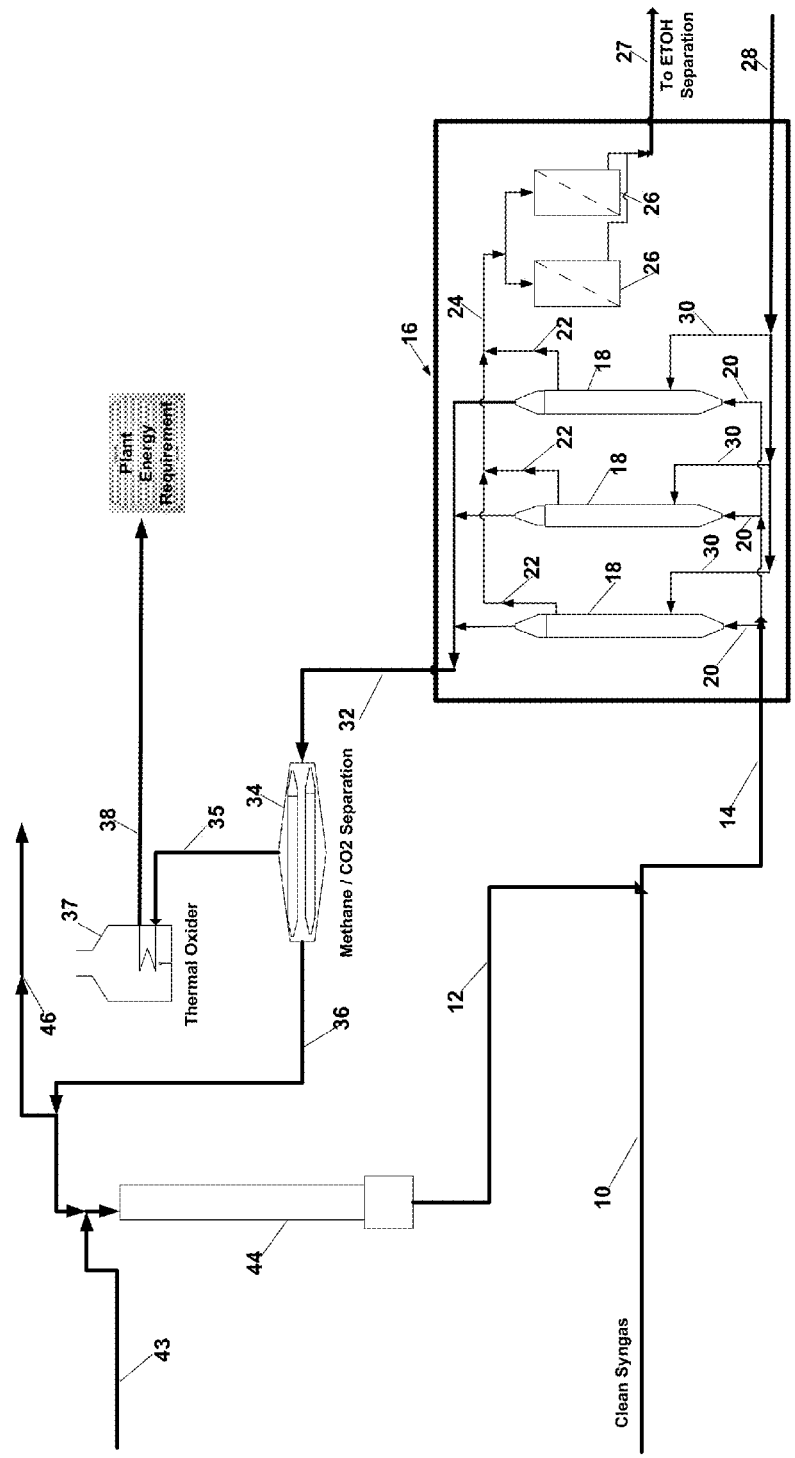
FIG. 1 is a schematic drawing of a process arrangement for biologically converting a methane containing syngas stream into liquid products in accordance with this invention.

FIG. 1 gives a general overview of the process and shows the major components of the process operation in simplified form. A stream of clean syngas enters the process via a line 10 and combines with a reformed syngas from a line 12 to provide a combined feed stream carried by a line 14 into a bioreactor section 16.

Line 14 feeds the combined syngas stream to a trio of bioreactors 18 via distribution lines 20. The syngas contacts the fermentation liquid in the bioreactors 18 and the microorganisms consume the CO, and CO2 and H2 and convert it into liquid products therein. A series of collection lines 22 withdraw fermentation liquid containing liquid products and cellular material from the microorganisms from each bioreactor 18. A line 24 transfers the fermentation liquid via a line 24 to purification zones 26. Before the fermentation liquid passes to a separation zone for the recovery of liquid products, in this case ethanol, the purification zone 26 removes biological materials and other dissolved matter. The purification zone may use any suitable means such as filtration or ultrafiltration to recover these materials. Microorganisms retained in the purification zone may be returned to the fermentor. After purification the rest of the fermentation liquid passes to an ethanol separation zone via a line 27. Fermentation liquid recovered from the ethanol separation zone returns to the bioreactors 18 via return line 28 and distribution lines 30.

A collection line 32 recovers the tail gas from bioreactors 18 and delivers it to a methane/CO2 separator 34. The separator effects a separation that produces an methane enriched stream taken by a line 36. The process does not have to reform all of the methane enriched stream. FIG. 1 shows the case where a line 46 takes a portion of the methane enriched stream for other use such as the supply of energy or for other conversion (not shown) A line 35 removes the CO2 rich stream from the separation process and delivers this stream to a Thermal Oxidizer/Steam generation equipment system 37. Hot exhaust gas or stream from Thermal Oxidizer goes to supply plant energy requirements. Alternatively the CO2 is also suitable for sequestration if desirable.

The line 36 carries the methane enriched stream to a partial oxidation autothermal reformer 44. Line 43 adds Oxygen, or enriched air, to the partial oxidation autothermal reformer. The autothermal reformer 44 converts the methane enriched stream and the oxygen stream into the additional syngas, consisting primarily of CO and H2. Line 12 takes the additional syngas for combination with the syngas carried by line 10 from the indirect gasification zone and make-up of the combined feed carried via line 14.

Indirect gasification systems are well known. (See U.S. Pat. Nos. 7,465,844 and 6,972,114.) This invention provides an advantage when using any type of gasification system to generate syngas that also generates significant amounts of methane. For purposes of this invention a significant amount of methane would equal 5% or more on an anhydrous basis. The process applies to higher concentration of methane in the syngas stream that can equal 10, 15, or 20% or more on an anhydrous basis.

One common form of indirect biomass gasification processes use a circulating fluidized bed process systems. Such systems generally consist of a biomass fuel feed system, two reaction vessels or chambers (gasification reactor & combustion reactor), and gas/solids separation equipment such as cyclones. Biomass fuel is fed into a gasification reaction chamber, using a solid feed handling system, at a continuous flow and a prescribed rate. In the gasification reaction chamber a circulating heat carrying/transfer material rapidly heats the biomass in an oxygen free environment converting it into syngas and char at approximately 850° C. and in any case preferably less than 900° C. While the indirect gasification zone can operate under a wide range of pressures from atmospheric to 11 bars absolute or more, it is preferable to operate the gasification section at a pressure compatible with the bioreactor system. Therefore pressures will usually be at least 4 bars absolute, but can go 11 bars absolute or higher. Usually the gasification zone gasifies the biomass under substantially anaerobic conditions. Substantially anaerobic conditions will mean an oxygen concentration of less than 1 mol % in the gasification reaction chamber. The syngas produced then transports the char and heat transfer material overhead and into a gas/solid separating system. This system separates the solids char and heat transfer material conveying the solids to the combustion reactor. The syngas exiting the separation system is the product syngas going to heat recovery and syngas cleanup as required.

In the combustion reaction chamber air is introduced which consumes the char, producing flue gas and ash, reheating the heat transfer material to approximately 1000 deg C. All of the remaining carbon is consumed in the combustion reaction chamber leaving a carbon-free ash. The heat transfer material, ash, and flue gas are transported overhead where the heat transfer material is separated from the flue gas and ash to be conveyed back to the gasification reaction chamber where it starts the process again. The ash is then separated from the flue gas leaving a clean hot gas stream that can be used for additional heat recovery.

Thus indirect or other related gasification technologies do not use direct combustion with oxygen or heating with plasma or molten glass etc. and do not have high temperature residence times. They have relatively high methane content. However they have good cold gas efficiencies in the 70 to 75% range.

As shown in Table 1 indirect gasification processes vary in the amount of methane, hydrocarbons and other syngas components they produce. Table 1 is a compilation from publicly available sources that show the typical gas compositions obtained from indirect gasification processes.

TABLE 1

Gas Compositions of several Indirect Gasification Processes

| Component, o/v | Taylor Gasification Process | FICFB | SilvaGas ® |
|---|---|---|---|
| Hydrogen | 45-48 | 37.7 | 20.7 |
| Carbon Monoxide | 15-20 | 29.1 | 46 |
| Methane | 10-13 | 10.4 | 15.6 |
| Ethylene | 1-3 | 2.8 | 5.3 |
| Carbon Dioxide | 18-20 | 19.6 | 11.1 |
| Ethane | 0-1 | 0.3 | 0.7 |
| Nitrogen | | trace | |

The syngas that now comprises CO, CO2, H2, methane, and a variety of other trace contaminates that requires clean-up prior to entering a bioreactor zone. The gas clean up can include removal of by products and residual hydrocarbons. Typical removal steps will extract any deleterious materials that would have any adverse effects with respect to the biological conversion zone. The syngas clean up typically involves removal of aromatic tars and minor contaminates such as particulates, H2S, HCl, etc can be removed if required.

One of these gasification technologies, namely the "Taylor" process claims to form syngas in a gasification reactor that is indirectly heated and then treated for the removal of tars. The syngas then passes through a gas conditioning reactor which produces a relatively tar free gas with the levels of non-condensibles in the product gas as shown in Table 1.

Lower temperature operation may lead to tar formation in the syngas. The aromatic tars reforming is usually included as part of the gasification process. One of these gasification technologies, namely the "Taylor" process claims to accomplish tar removal in situ within the gasification system or using a downstream catalytic process. In the case of lower temperature gasification tar elimination may not take place nor will recycling of the methane back to the gasifier lead to substantial conversion to CO or H2. The short residence time in the hot temperature zone of these indirect gasifiers typically does not provide suitable conditions for the conversion of the methane. Therefore this invention leads to true conversion of the methane that will then be converted to liquid products in the bioreactor.

When using wood chips and most other biomass fuel sources, the removal of the other minor source contaminates is not expected to be complicated and can be achieved with standard scrubbing systems. Heat recovery systems are usually installed between the aromatic tars reforming and the remaining gas clean up systems where steam or hot water can be generated to benefit on-site energy requirements.

This invention may be applied to any bioconversion process that produces an aqueous stream containing a dilute concentration of ethanol. Bioconversions of CO and H2/CO2 to acetic acid, n-butanol, butyric acid, ethanol and other products are well known. For example, in a recent book concise description of biochemical pathways and energetics of such bioconversions have been summarized by Das, A. and L. G. Ljungdahl, Electron Transport System in Acetogens and by Drake, H. L. and K. Kusel, Diverse Physiologic Potential of Acetogens, appearing respectively as Chapters 14 and 13 of Biochemistry and Physiology of Anaerobic Bacteria, L. G. Ljungdahl eds., Spring er (2003). Any suitable microorganisms that have the ability to convert the syngas components: CO, H2, CO2 individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid and *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351. All of these references are incorporated herein in their entirety.

The microorganisms found suitable thus far for this invention require anaerobic growth conditions. Therefore the system will employ suitable control and sealing methods to limit the introduction of oxygen into the system. Since the organisms reside principally in contact with the liquid volume of the retention chamber the system maintains a suitable redox potential in the liquid and this chamber may be monitored to make insure anaerobic conditions. Anaerobic conditions in the retained liquid volume are usually defined as having a redox potential of less than −200 mV and preferably a redox potential in the range of from −300 to −500 mV. To further minimize exposure of the microorganisms to oxygen the feed gas will preferably have an oxygen concentration of less than 1000 ppm, more preferably less than 100 ppm, and even more preferably less than 10 ppm.

The instant invention can use any type of bioreactor to retain the microorganisms for the conversion of the syngas. Many devices and equipment are used for gas transfer to microorganisms in fermentation and waste treatment applications. Conventional systems will retain a substantial volume of fermentation liquid in a vessel or column and use means for agitation to promote mass transfer between the relatively insoluble syngas components and the microorganisms retained in the fermentation liquid. In application of this invention to the production of liquid products from gas streams, in particular CO or a mixture of CO2 and H2 the liquid column will typically comprise a bioreactor that retains microorganisms suspended in a fermentation liquid. Specific types of bioreactors include bubble column bioreactors and stirred tank bioreactors. These conventional bioreactors and systems may use agitators with specialized blades or configurations to create a continuous stirred reactor. Other system use gas lift or fluidized beds, liquids or where gases are circulated via contacting devices. The fluidized systems are generally configured for use with microorganisms in planktonic form i.e. they exist as individual cells in liquid medium. Gas dissolution rates for such systems are also generally low.

Cell retention by formation of biofilms is a very good and often inexpensive way to increase the density of micro organisms in bioreactors. This requires a solid matrix with large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. They suffer from either being very large or unable to provide sufficient gas dissolution rates.

The use of bioreactors that retain biofilms has been proposed for the production of liquid fuels. US Applications 20080305539 and 2009029434 shows the use of a bioreactor to support microorganisms on or in a membrane (preferably hollow fiber membranes) for the production of ethanol from syngas. US Application 20090035848 shows the use of bioreactor for producing ethanol from syngas using microorganisms retained on media that circulates as a moving bed in a fermentation liquid. In both of these bioreactors the fermentation liquid retains the ethanol from the microorganisms in dilute concentration.

All these systems for conversion of biomass derived syngas rely on a fermentation broth that provides a low concentration of ethanol in a relatively large volume of aqueous liquid. Ethanol concentration will ordinarily fall below 6% and in most cases less than 4%. As a result practical recovery of ethanol from the fermentation broth requires a separation system that can efficiently recover the ethanol from the dilute fermentation liquid.

Depending on the nature of the liquid product produced, there are a number of technologies that can be used for product recovery. Methods for recovering ethanol from fermentation liquids are well known and include traditional distillation methods. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products. U.S. Pat. No. 6,899,743 B2 and U.S. Pat. No. 6,755,975 B2 disclose processes for recovering organic compounds such as ethanol from water by the use of pervaporation followed by dephlegmation.

In addition to low concentrations of ethanol, the fermentation liquid as with any biological process will contain other dissolved and undissolved components. Such components include cells, proteins, salts, unfermented solubles and colloidal materials. These materials can impose impurities into the separation processes thereby requiring additional separation steps and purification steps for the recovery of ethanol or other liquid products.

In addition to producing liquid products, the fermentation zone effects the separation of the methane from the other syngas components. The production of the liquid products in the fermentation zone uses the high degree of conversion and selectivity of the fermentation process to effect recovery of the methane from the syngas by high conversion of the CO and H2/CO2 from the entering syngas. This conversion produces a tail gas for removal from the process that consists mainly of CO2 and CH4.

For example a typical high methane syngas feed composition of: CO 30%, H2 30%, CH4 15%, CO2 20% and other HC 5% when fed to a bioreactor for producing ethanol that achieves a 90% conversion of the CO and H2/CO2 will produce a high methane feed. In this case for every 100 moles of total gas fed, the tail gas will be: CO-3 moles, H2-3 moles, CO2-29 moles, CH4-15 moles and HC-5 moles. Thus the composition of this gas in mole or volume % will be: CO-5.45%, H2-5.45%, CO2-52.73%, CH4-27.27% and HC-9.09%. Methane and HC will have ~93% of the energy content of this tail gas. The CO2 has no energy value and has to be removed from the process. Also noteworthy is that this tail gas is typically at a temperature of ~37 C and its pressure can be in the range of 5 to 50 psig. For example a typical membrane supported bioreactor technology can operate at feed gas pressures in the range of 100 psig and the exhaust gas will be in the range of 50 psig. Therefore these pressures and temperatures are in a range that facilitates incorporation with downstream separation steps.

This separation and removal of the CO2 after the bioreactor is an important step in this process invention and the compatibility of these temperatures promotes integrated with the typical process operating conditions, which are moderate pressures (3 to 7 atmospheres) and temperatures (35 to 50 C). The primary separation needs to be between CH4/HC and CO2.

Separation of CO2 from predominantly methane and the HCs and most of the CO and H2 can be done by several technologies such as absorption desorption, scrubbing/extraction by amines, or membranes. U.S. Pat. No. 5,558,698, U.S. Pat. No. 4,597,777 and the references described therein disclose a number of membranes and methods for effecting such separations. The membrane based technologies may be particularly suitable because of their modularity and operability at the temperatures and pressures provided. Since the CO2 separation is not required at high levels and separation of approximately 70% or greater is acceptable, membrane systems are ideal process systems to meet these requirements. There are several companies that can provide membrane systems to meet these requirements (Air Liquide, Air Products, Guild Associates, etc.) In addition recent advances in certain zeolite adsorbents where the pore size has been reduced from 4 A to 3.7 A has led to the "Molecular Gate" technology where CH4 and HC are blocked from entering the pores whereas the CO2 and other smaller gas molecules are adsorbed and readily separated. This technology, originally developed by Englehard Corporation is licensed by Guild Associates (Dublin, Ohio). More information on this technology: Guild Associates—www.moleculargate.com.

Classic amine and methanol based extraction technologies are also suitable and several operate at moderate pressures and near ambient conditions. The CO2 that will be desorbed from the regeneration of the amine extract will be essentially free of combustible gasses and can be vented or used for CO2 applications.

The CO2 may also find application within the plant itself. Since the preferred gasification systems for this invention will normally operate under oxygen starved conditions an inert purge medium routinely enters the feed system to displace air that could enter with the feed. The recovered CO2 can provide a ready source for the purge medium.

After conversion of the CO and H2 and separation of CO2 the tail gas stream leaves a methane rich stream containing some remaining CO2 and residual hydrocarbons. These separation technologies can recover as high as 95 mol % of the CH4 and hydrocarbons as well as some of the residual H2 and CO. While high removal of the CO2 may have the advantage of reducing mass flow, it is not necessary to achieve essentially complete removal of all CO2 for the effective practice of this invention. A rough cut separation can work as well as long as the CO2 concentration in the methane rich stream reaches a steady state concentration that does not inhibit its use in generating power or providing methane for reforming and producing products.

Allowing higher quantities of CO2 to remain with the methane stream may provide the advantage of lowering oxygen requirement for partial oxidation reforming of the methane. This CO2 can supply part of the oxygen requirement. Thus the process can benefit from having as little as 5 mole % CO2 in the methane enriched stream and amounts or 10 mole %, up to about 30 mole % CO2 in the methane enriched stream can be beneficial. Amounts of CO2 in the methane enriched stream that exceed 30 mole % can start to reduce the conversion of methane in the partial oxidation reformer.

The methane rich stream can be used for several purposes. The principal purpose in keeping with this invention is to generate additional liquid products. To this end the process will partially oxidize and reform the methane, using partial oxidation to produce additional feed for conversion in the bioreactor. In keeping with this invention at least a portion of the methane rich stream will go to produce additional liquid products. The next step in producing additional products reforms the methane rich stream into good quality syngas containing predominantly CO and H2/CO2 for recycle to the bioreactors.

The type of methane reforming will depend on a variety of factors but may be in large part be dictated by the amount of methane recovered for conversion. Steam reforming of methane is a very common method of producing large quantities of hydrogen as well as CO. In typical ammonia production applications a water gas shift reaction is also employed to further increase the production of hydrogen. Such processes are capital intensive, operate at high temperatures (700-1100° C.) and usually in the presence of a nickel-based catalyst. Steam is included in the reversible reactions.

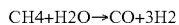

$$CH_4 + H_2O \rightarrow CO + 3H_2$$

Since the production of CO and H2 is endothermic in nature this reaction will typically produce high amounts of CO2.

In one embodiment, the process will use partial oxidation autothermal reforming (ATR) sometimes referred to as oxygen fired reforming. In ATR Syngas is produced using oxygen, CO2 and sometimes steam in a reaction with methane. Typically, a single chamber houses a combustion zone where partial oxidation of methane produces the heat necessary heat for the reaction.

The well known partial oxidation autothermal reforming reaction when using CO2 is—

$$2CH_4 + O_2 + CO_2 \rightarrow 3H_2 + 3CO + H_2O + Heat$$

Typical syngas from the process will have an outlet temperature of between 850-1100 C and the outlet pressure can be up to 11 bars absolute.

This invention does not require that all of the recovered methane get converted to liquid products. A certain amount of the methane rich stream may be use to generate power. For example a thermal oxidizer steam generator may receive a portion of the methane enriched stream. Since the methane rich stream has a high fuel value it can be alternately be used for other plant energy requirements. Thus, this invention provides a simple way of isolating the methane rich stream and having it available for use as a feed to produce additional liquid products or as a source of energy to supply power for plant operations.

Figure 2:
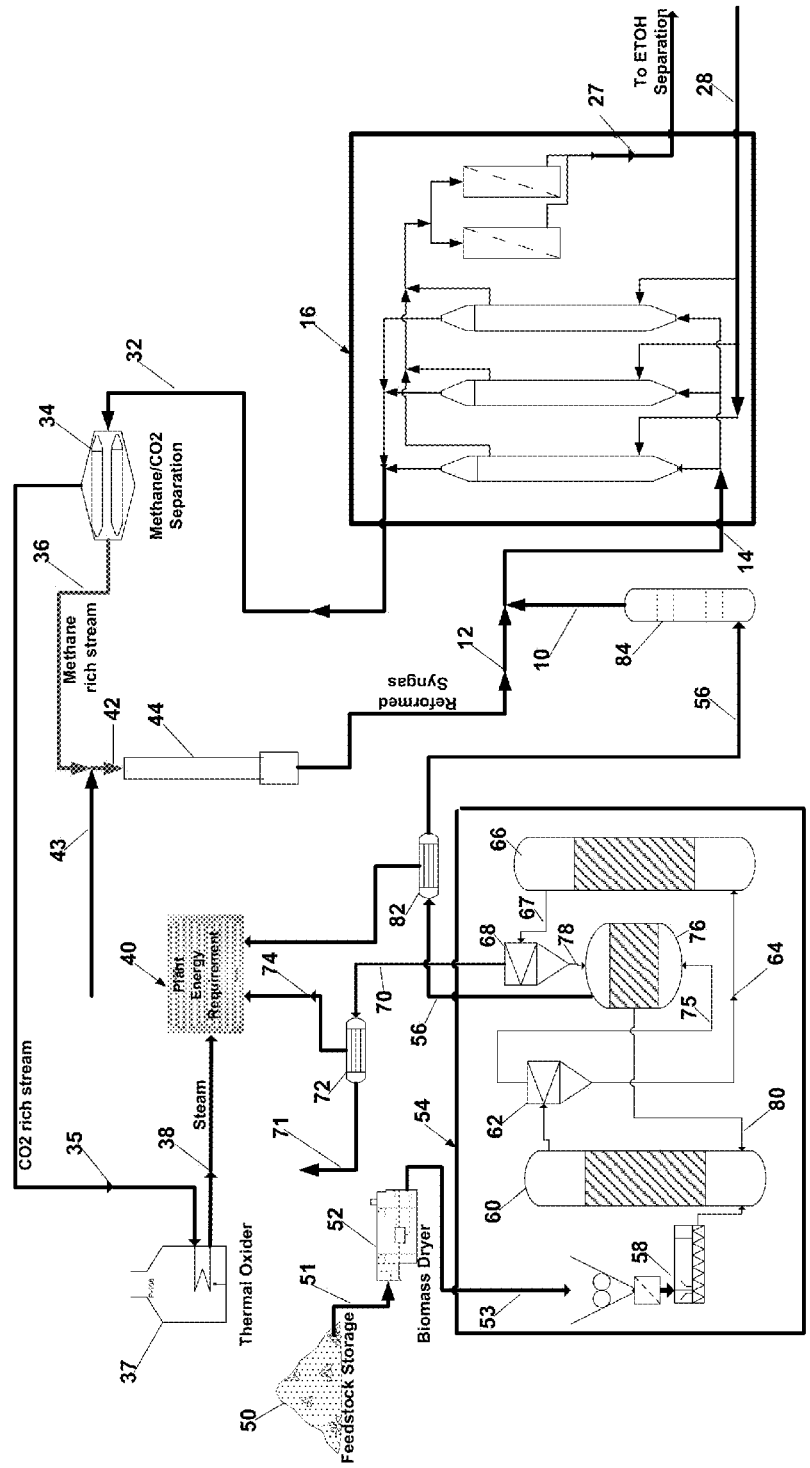
FIG. 2 is a schematic drawing of a process arrangement showing the generation of syngas from biomass and the biological conversion of a methane containing syngas stream into liquid products in accordance with this invention.

FIG. 2 provides a more complete description of the invention with in the context of a descriptive flow diagram. FIG. 2 shows woody biomass 50 as the starting material. Transfer lines 51 and 53 convey the woody biomass to the solids transport system 58. The woody biomass has about 20% moisture content prior to entering the indirect gasification process section 54. If necessary, the woody biomass may pass through an optional drier 52 to adjust its moisture content.

The indirect gasification section converts the woody biomass into the primary syngas stream carried by a line 56. Within the gasification section a solids transport system 58 conveys the woody biomass at a continuous controlled rate to the gasification reaction chamber 60 where hot bed media intensely contacts the biomass to produce a pyrolysis syngas and char. The char and media solids, along with the syngas flow out of the top of chamber 60 and into a solids separation system 62 that separates the pyrolysis syngas stream from the char and heat transfer (HT) media. The char and HT media flow from separation system 62 via a line 64 and into a combustion reaction chamber 66 where the char is combusted with air in the presence of the hot media. An additional solids separation system 68 receives the flowing mixture of gas and solids from combustion reactor 66 via a line 67 and the system separates the combustion gas from the solids. The combustion exhaust gas gets carried overhead by a line 70 for recovery of heat in a waste heat recovery boiler 72 that generates steam carried by a line 74 for supply to plant equipment 40 and the cooled combusted is taken for venting via line 71.

The pyrolysis syngas taken overhead from separation system 62 via a line 75 flows into a conditioning reactor 76 (for the removal of in situ tars as in the Taylor Gasification Process) where it mixes with the hot media that flows downward from solids separation system 68 via line 78. The conditioning reactor converts the heavy hydrocarbon (tars) components of the pyrolysis syngas by contact with the hot media. After contact with the syngas the hot media is recycled to the gasification reaction chamber 60 via line 80. Syngas is recovered from the contact reactor via the line 56 and has an estimated composition on anhydrous basis of: CO 30%, H2 30%, CH4 15%, CO2 20% and other HC 5%.

The syngas undergoes further conditioning before entering the bioreactor section 16. The syngas typically at a temperature of 800 to 1000 C and at pressures of 100 psig is cooled to about 40 C by a series of heat exchangers and the steam is recovered for power and energy production. Heat exchangers 82 produce additional steam to supply of steam taken by line 83 for plant equipment 40. The cooled gas is further scrubbed with aqueous fluids and filtered to remove particulates and residual tarry materials in syngas clean-up section 84.

The clean syngas is now fed in the manner previously described with respect to FIG. 1 to a series of bioreactors via line 10. The bioreactors again contain the microorganisms that convert the CO and H2/CO2 to the desired liquid products. Bioconversion processes can use the CO and H2/CO2 from the feed syngas and convert it to the desired products with a high degree of conversion and selectivity. For example using strains of the microorganisms such as C. Ragsdali C. Ljungdahli, C. autoethanogenium the CO and H2/CO2 can be converted to ethanol with almost 95% of the theoretical selectivity as shown in the following equations.

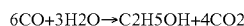

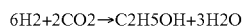

With the syngas feed composition described earlier of: CO 30%, H2 30%, CH4 15%, CO2 20% and other HC 5% fed to a bioreactor and 90% conversion of the CO and H2/CO2 producing ethanol, for 100 moles of total gas fed, the tail gas will be: CO-3 moles, H2-3 moles, CO2-29 moles, CH4-15 moles and HC-5 moles. Thus the composition of this gas in mole or volume % will be: CO-5.45%, H2-5.45%, CO2-52.73%, CH4-27.27% and HC-9.09%. Methane and HC will have ~93% of the energy content of this exhaust gas. The CO2 has no energy value and has to be removed from the process. The fermentation liquid passes to ethanol separation zone via line 27 and recovered fermentation liquid returns to the bioreactors via line 28.

The tail gas having the composition given above passes via line 32 to the methane/CO2 separator 34 for removal of CO2 and concentration of the methane and hydrocarbon components. Separator 34 uses membrane separation technology (Air Liquide, Air products, Guild Associates, etc) or a combination of membrane separation and adsorption-desorption technology operated at pressures around 5 to 7 atm and at near ambient temperatures. These technologies can also be assembled in small to medium scale systems. For example "Biogas" from anaerobic digesters which contains ~60% CH4 and ~40% CO2 can be upgraded to >90% CH4 and the CO2 removed and exhausted.

In the methane/CO2 separator 34 the tail gas from the bioreactor is further compressed (if necessary) and fed to membrane separation combined with a pressure swing adsorption desorption system that contains the aforementioned "Molecular Gate" zeolite adsorbents where the pore size has been reduced from 4 A to 3.7 A and CH4 and HC are blocked from entering the pores whereas the CO2 and other smaller gas molecules are adsorbed and readily separated. This technology readily recovers up to >95% of the CH4 and HC in a methane rich stream taken via line 36 and a separated CO2 rich stream taken via line 35. The typical composition of the methane rich stream based on 95% CO2 separation and 100 moles of bioreactor exhaust gas fed is: CH4-25.9 moles, HC-8.7 moles, CO2-2.6 moles, CO-0.27 moles and H2 0.27 moles. The CO2 rich stream the corresponding composition is: CO2-50.1 moles, CH4-1.4 moles, HC-0.4 moles, CO 5.2 moles and H2-5.2 moles. These compositions vary based on the CO2 separation technique. The minor impurities namely H2S will also be separated and go with the CO2 stream. The CO2 rich stream may be combined with other exhaust gas streams (not shown) and fed to a thermal oxidation system 37 via line 35 to recover its combustion energy to generate steam after which it is exhausted to the atmosphere.

Line 42 feeds the methane rich stream to the partial oxidation reformer 44 where the requisite amount of oxygen via line 43 is added and it is converted to produce CO and H2/CO2. The methane rich stream described earlier will be of a general composition of (in mole %): CH4 and HC-91.6%, CO2-6.9%, CO-0.7% and H2-0.7%. This is fed to the partial oxidation reformer together with oxygen. Typically the mole ratio of methane plus other hydrocarbons to oxygen (HC/O2 ratio) can range from will be at least 1.8 to 1 and depending on the quantity of CO2 in the methane rich stream the HC/O2 ratio can go as high as 4 to 1 or more and having a higher percentage of the CO2 in the methane enriched stream can, as previously explained, decrease the amount of oxygen needed for addition to the partial oxidation reformer. The oxygen can be pure oxygen from a liquid oxygen source or enriched oxygen from a pressure swing air separation process. The partial oxidation reformer is operated around 850 C to 1100 C and 100 psig pressure. The product gas composition is approximately (in mole %): CH4-1%, H2-60%, CO-33%, CO2-1.5% and H2O2O-4.5%. Thus the methane rich stream can be almost quantitatively converted in the partial oxidation reformer to make H2 and CO which are both convertible to the liquid products by the microorganisms. This reformed gas is added to the bioreactor section 16 via line 12 and 14 together with the primary gas carried by line 10 from the gasifier in a continuous integrated process as shown in the FIG. 2.

Any excess gas from the methane rich stream is taken by line and used to supply plant energy needs. In addition to the use the methane rich stream to supply plant energy requirements via equipment 40. FIG. 2 shows the optional use of a thermal oxidizer steam generator that can optionally receive the CO2 stream.

The invention claimed is:
1. A process for the production of liquid products from a biomass feedstock by indirect gasification to syngas comprising $CO_2$, CO, $H_2$ and $CH_4$, and bio-conversion of syngas components, said process comprising:
providing a biomass feedstock to a gasifier and indirectly gasifying the biomass feedstock by contact with a heating medium to produce a syngas stream comprising $CO_2$, CO, $H_2$ and at least 10 mole % $CH_4$ on an anhydrous basis;

passing a feed gas comprising the syngas stream and containing at least 10 mole % $CH_4$ on an anhydrous basis from the gasifier to a bioreactor to convert CO and $CO_2$ and $H_2$ to liquid products by contact with microorganisms therein;

withdrawing a bioreactor effluent stream containing the liquid products from the bioreactor and recovering liquid products from the bioreactor effluent stream;

recovering a tail gas stream from the bioreactor comprising $CO_2$ and $CH_4$;

separating $CO_2$ from the tail gas stream to produce a $CH_4$ rich gas stream;

passing at least a portion of the $CH_4$ rich stream to a reformer to produce a reformed stream comprising CO and $CO_2$ and $H_2$; and, passing at least a portion of the reformed stream to the bioreactor along with syngas from the gasifier to provide the feed gas to the bioreactor.

2. The process of claim 1 wherein the liquid products comprise at least one of ethanol, acetic acid, butanol, or butyric acid.

3. The process of claim 1 wherein a portion of the $CH_4$ rich stream passes to a combustion heat recovery system for the generation of power or to provide process heat.

4. The process of claim 1 wherein the gasifier comprises a gasification zone that gasifies the carbonaceous feed under substantially anaerobic conditions and a combustion zone that provides heat to the gasification zone.

5. The process of claim 1 wherein the oxygen concentration in the gasification zone is less than 1 mole %.

6. The process of claim 1 wherein the reformer comprises a partial oxidation autothermal reformer.

7. The process of claim 1 wherein the syngas undergoes clean-up for removal of water and particulates before entering the bioreactor.

8. The process of claim 1 wherein the biomass is selected from one or more the group consisting of wood, miscanthus, switchgrass, sugar cane bagasse, corn stover and urban waste.

9. The process of claim 1 wherein the liquid products comprise ethanol.

10. The process of claim 7 wherein the microorganisms in the bioreactor comprises a mono-culture or a co-culture of at least one of *Clostridium ragsdalei, Butyribacterium methylotrophicum, Clostridium Ljungdahlii, Clostridium Autoethanogenum, Clostridium Woodii* and *Clostridium carboxydivorans*.

11. The process of claim 1 wherein the syngas on an anhydrous basis comprises 20 to 45 mole % $H_2$, 15 to 50 mole % CO, 10 to 20 mole % $CH_4$, and 10 to 20 mole % $CO_2$ and the tail gas comprises at least 25 mole % $CH_4$ and at least 50 mole % $CO_2$.

12. The process of claim 1 wherein the gasifier operates with a temperature of less than 900° C. and a pressure of less than 4 bars absolute.

13. A process for the production of ethanol from a biomass feedstock by indirect gasification to syngas comprising $CO_2$, CO, $H_2$ and $CH_4$, and bio-conversion of syngas components, said process comprising:

providing a biomass feedstock to a gasifier and indirectly gasifying the biomass feedstock by contact with a heating medium at a temperature of less than 900° C. and a pressure of less than 4 bars absolute to produce a syngas stream comprising $CO_2$, CO, $H_2$ and at least 10 mole % of $CH_4$ on an anhydrous basis;

passing a feed gas comprising syngas and containing at least 10 mole % $CH_4$ on an anhydrous basis from the gasifier to a bioreactor to convert CO and $CO_2$ and $H_2$ to ethanol by contact with microorganisms therein;

withdrawing a bioreactor effluent stream containing ethanol from the bioreactor and separating the ethanol in a ethanol recovery section to produce an ethanol product;

recovering a tail gas stream from the bioreactor comprising on an anhydrous basis at least 40 mole % $CO_2$ and 25 mole % $CH_4$; separating $CO_2$ from the tail gas stream to produce a $CH_4$ rich gas stream;

passing a portion of the $CH_4$ rich gas stream to a combustion heat recovery system for the generation of power or to provide process heat;

passing at least a portion of the $CH_4$ rich stream to an autothermal reformer to produce a reformed stream comprising CO and $CO_2$ and $H_2$; and, passing at least a portion of the reformed stream to the bioreactor along with syngas from the gasifier to provide the feed gas to the bioreactor.

* * * * *